United States Patent
Otjes et al.

(10) Patent No.: US 7,830,508 B2
(45) Date of Patent: Nov. 9, 2010

(54) METHOD AND ASSEMBLY FOR DETERMINING SOOT PARTICLES IN A GAS STREAM

(75) Inventors: René Paul Otjes, Schagen (NL); Laura Hernández Alpizar, San José (CR)

(73) Assignee: Stichting Energieonderzoek Centrum Nederland, Petten (NL)

( * ) Notice: Subject to any disclaimer, the term of this patent is extended or adjusted under 35 U.S.C. 154(b) by 323 days.

(21) Appl. No.: 11/813,815

(22) PCT Filed: Jan. 12, 2006

(86) PCT No.: PCT/NL2006/050007

§ 371 (c)(1),
(2), (4) Date: Apr. 1, 2008

(87) PCT Pub. No.: WO2006/091095

PCT Pub. Date: Aug. 31, 2006

(65) Prior Publication Data

US 2008/0198382 A1 Aug. 21, 2008

(30) Foreign Application Priority Data

Jan. 12, 2005 (NL) .................................... 1028013

(51) Int. Cl.
*G01N 15/02* (2006.01)
(52) U.S. Cl. ..................................................... 356/335
(58) Field of Classification Search .......... 356/335–343
See application file for complete search history.

(56) References Cited

U.S. PATENT DOCUMENTS

| 6,217,636 | B1 | 4/2001 | McFarland |
| 6,503,758 | B1 | 1/2003 | Allen et al. |
| 2002/0134137 | A1 * | 9/2002 | Ondov et al. ............... 73/28.05 |

FOREIGN PATENT DOCUMENTS

| CH | 615 998 A5 | 2/1980 |
| GB | 2 320 088 A | 6/1998 |
| WO | WO 98/43063 A | 10/1998 |
| WO | WO 02/18911 A | 3/2002 |

* cited by examiner

*Primary Examiner*—Michael P Stafira
(74) *Attorney, Agent, or Firm*—Sughrue Mion, PLLC

(57) ABSTRACT

Method and assembly for determining the presence of soot particles in a gas stream such as in the air. To prevent the disturbing effect of salts and the like that may be deposited on soot particles, it is proposed to introduce the soot particles into water as a suspension. The salts concerned dissolve in the water and have no effect when determining the change in optical properties resulting from the presence of the soot particles. This determination comprises in particular a light transmittance measurement. The presence of the soot particles can be determined after the gas stream is first passed through a filter, as a result of which a particle size distribution can be determined.

Suspension of the soot particles can be achieved by subjecting these to a stream of steam, whereby the steam condenses on the soot particles and then causes these to precipitate out of the gas. The various processes can be expedited by using a cyclone.

10 Claims, 3 Drawing Sheets

METHOD AND ASSEMBLY FOR DETERMINING SOOT PARTICLES IN A GAS STREAM

The present invention relates to a method for determining soot particles in a gas stream, comprising the measurement of the optical properties.

Such a method is generally known in the art and is carried out, for example, in a so-called aethalometer. Soot particles occur in the atmosphere as an undesired component. Among other sources, these originate from diesel engines. It has been found that the determination of suspended soot particles in air and other gaseous media is unpredictable because of the other particles adhering to the soot. Particularly large measurement differences have been found especially if the measurement is based on the transmittance of light, as a result of which it is impossible to determine the soot concentration rapidly and accurately with existing meters.

Such an accurate determination is important. Soot particles are in fact harmful to human and animal airways. This is especially true of soot particles with a particle size between a few nanometres and a few micrometres. More particularly it is important to measure the presence of soot particles with dimensions smaller than 400 nm. Such particles can occur in very small concentrations. For example, a value of some $\mu g/m^3$ gas may be mentioned.

As a result of the presence of deposits on the soot particles, unpredictable effects during the irradiation of the soot particles with light arise. Scattering is one such observed effect. Because of this, serious accurate measurement is impossible.

A method for determining atmospheric pollutants is disclosed in GB 2 320 088. More in particular, the size distribution of such pollutants can be determined by passing the atmospheric gas through fluid columns connected in series, a certain particle size being absorbed in each column.

A method for determining pollutants present in the atmosphere by the collection of an aerosol is disclosed in U.S. Pat. No. 6,503,758.

The aim of the present invention is to provide a method with which it is possible to determine the presence of soot particles in an accurate manner. More in particular, the aim of the present invention is to provide a method which can be carried out continuously or discontinuously. Furthermore, one aim of the present invention is to prevent effects caused by soluble salts in the light measurement as far as possible.

This aim is achieved with a method as described above in that said soot particles in said gas stream are moistened and then introduced into a liquid that dissolves salts and the optical properties of said soot particles/liquid suspension are determined.

According to the present invention the determination of the optical properties no longer takes place in a gas stream, such as air, containing soot particles, but in a liquid. The soot particles are brought into suspension in that liquid. It has been found that of the "foreign" particles adhering to the soot, at least 70% is a soluble salt. These salts dissolve in the liquid and the detrimental disturbing effect of these foreign particles will largely be eliminated. It has been found that with the invention the time resolution considerably increases, for example from 1 day to 1 minute.

Suspension of the soot particles in the liquid can be carried out by any means known in the state of the art.

According to the invention the soot particles are moistened with the liquid concerned or a liquid related thereto. This moistening can be carried out by a physical (condensation) or chemical means. The mass of the soot particles thereby increases and it is possible to separate the soot particles from the gas with separation on a weight basis. For example, using a centrifuging operation with, for example, a cyclone the soot particles collect in the liquid used.

If the liquid comprises water, the moistening can be carried out by passing a (water) vapour stream through the gas containing soot particles to be determined.

The suspension achieved with the invention has proved particularly stable. It is consequently possible to prepare the suspension at a measurement location and then to measure this at another place, such as a central laboratory, in a sealed container. However, it is also possible to carry out measurements on the spot on a continuous basis.

According to a further advantageous embodiment of the invention the soot particles are first passed through a filter before they are subjected to a determination. Soot particles of a certain particle size are thereby retained. By using filters with different permeabilities, different determinations can be performed and on this basis a statement can be made not only about the amount of soot present, but also about the particle size distribution. As previously stated, this is important as in certain determinations the larger particles in particular are less important. Thus, in certain measurements, a statement is especially requested regarding the amount of particles with a particle size of less than 2.5 µm.

The invention also relates to a assembly comprising the determination of the soot particle size distribution in said gas stream, wherein for carrying out the method described above the gas stream is passed as described above through a first filter, followed by a first determination as described above, and is then passed through a second filter with a different permeability to the first filter for performing a second determination according to the above method. This stage can be repeated a number of times to achieve a highly refined particle size distribution.

Various measures can be taken to keep the measurement device in particular clean. For instance, it is possible to flush this regularly with a separate flushing liquid. It is also possible to pass through gas bubbles.

The invention will be explained in more detail below with reference to an illustrative embodiment shown in the drawings. In the drawings.

In the figures, the assembly according to the invention is indicated in its entirety by 1. This consists of a measurement device 2, a suspension device 3 and a filter unit 4. A moistening device 18 is connected between the suspension device 3 and filter unit 4.

Figure 1:
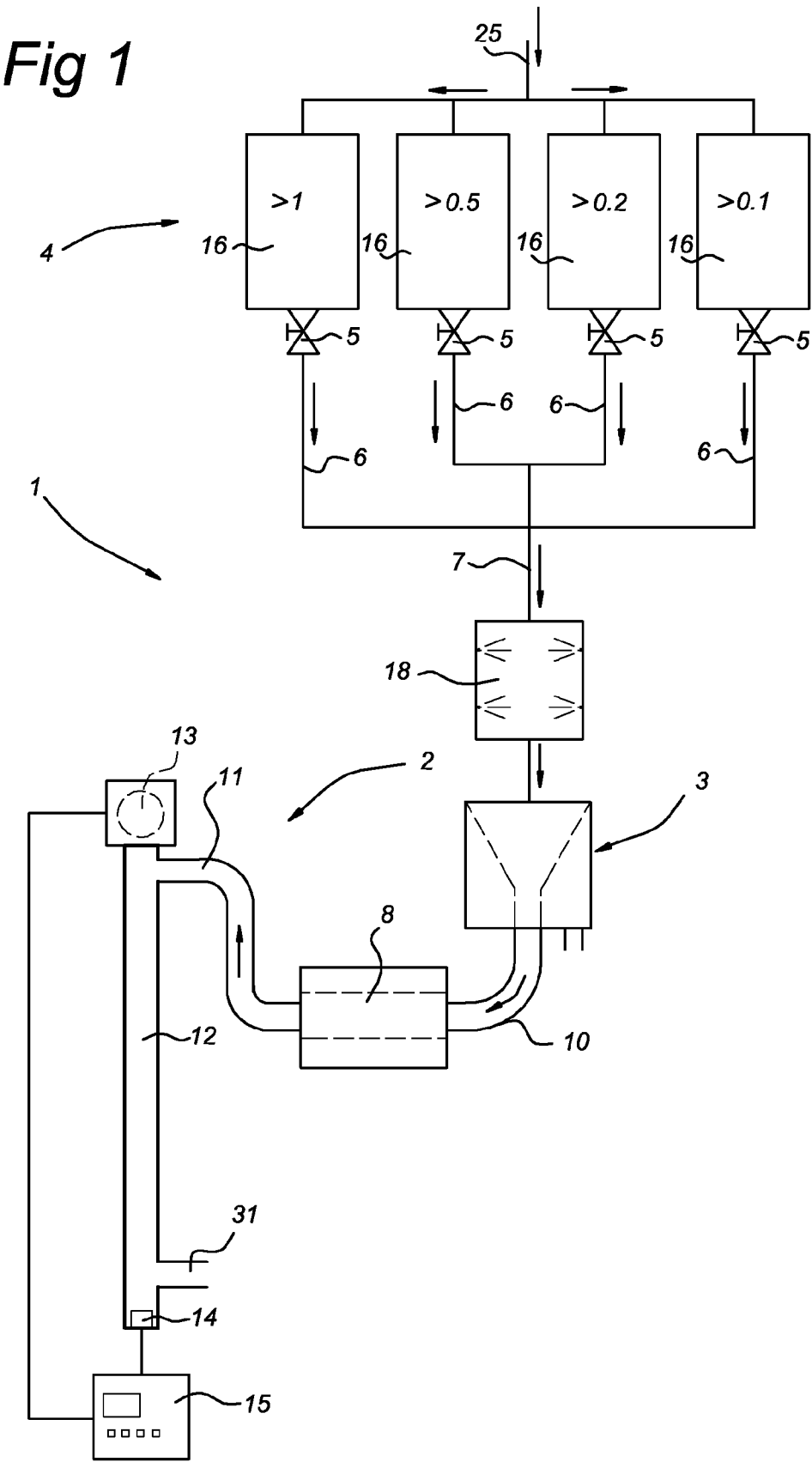
FIG. 1 shows highly diagrammatically the layout of a measurement assembly according to the invention.
Figure 2:
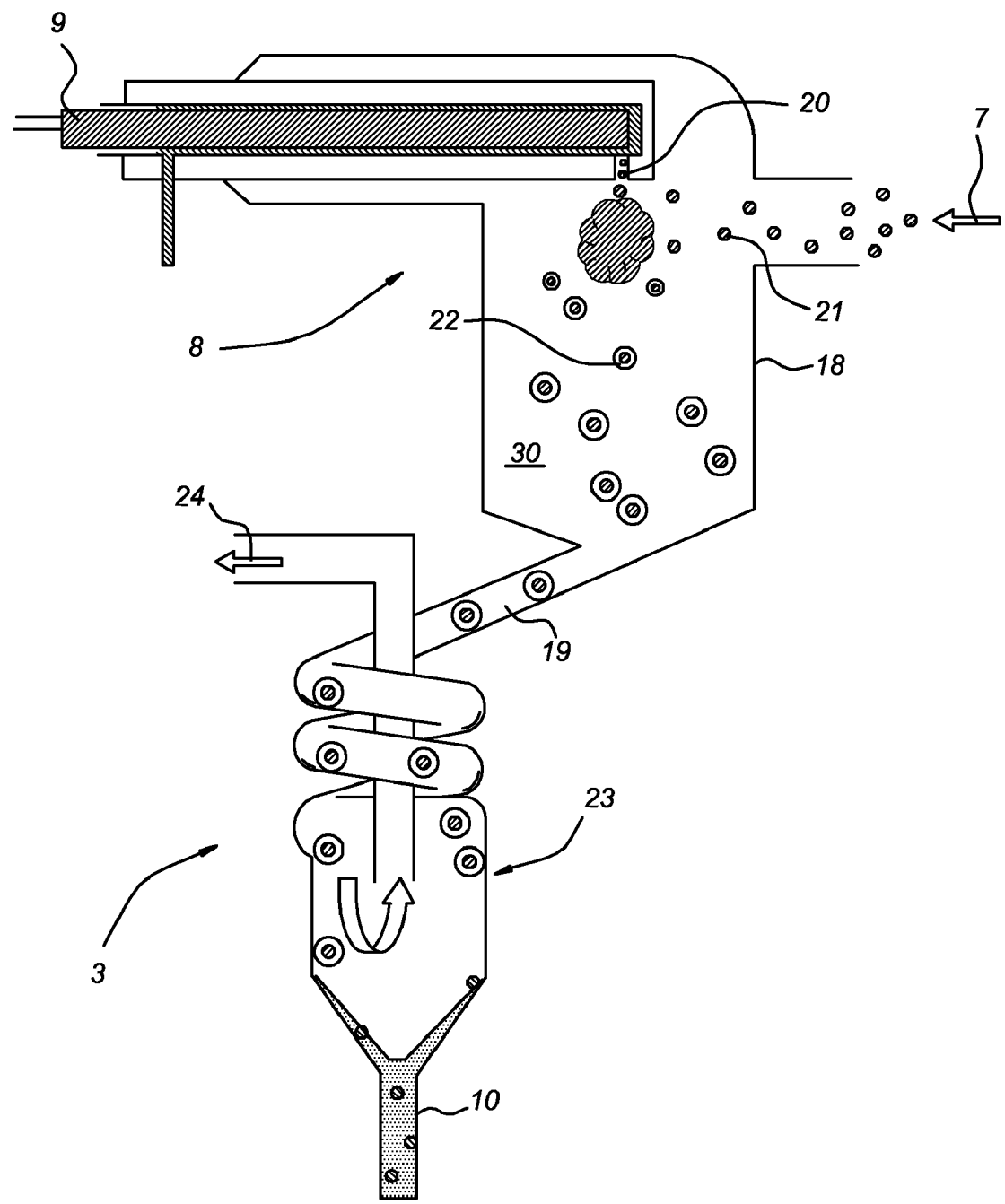
FIG. 2 shows details of the suspension device and moistening device according to the invention.

The filter unit 4 consists of a number of filters 16. These preferably have a different permeability and a shut-off valve 5 is always connected downstream thereof. As an example, a filtering limit for the filters of 0.1; 0.2; 0.5 and 1 µm, respectively, is mentioned. This means that particles larger than the value concerned are not allowed through. The gas to be measured wherein in soot particles are present is fed via inlet 25. Depending on the operational circumstances, one (or more) of the shut-off valves 5 will be opened, though which the particular gas introduced is fed after filtering via pipe 6 and common discharge pipe 7 to moistening device 18. The gas with moistened soot particles is then introduced into the suspension device 3, the details of which are shown in FIG. 2. Separation of the gas and soot particles takes place there. The soot particles are passed through a degassing device 10 and fed via pipe 11 to measuring tube 12 of measurement device 2. Measuring tube 12 is provided at one end with a lamp or some other lighting device 13 and provided at its other end with a sensor 14. The electronic part of the measurement device, which may also include a controller, is indicated by 15. The measuring tube 12 can have a relatively small volume of e.g. 0.2 ml for a length of about 1 metre.

FIG. 2 shows details of the suspension device 3 and the moistening device 18. The gas originating from the filters 16 enters the moistening device 18 via pipe 7. Steam is injected into the chamber 30 through nozzle 20 via pipe 9. As shown diagrammatically here, liquid 22 collects around the soot particles 21. Moreover, some agglomeration of the particles thus obtained occurs. Consequently, the weight thereof in the moistening device 18 increases considerably. The particles moistened in this way are fed to suspension device 3 via inlet pipe 19. This device consists of a cyclone 23 with a central outlet 24 for gas extending upwards. This gas is extracted with a gas pump. Liquid with soot particles collects at the wall of cyclone 23 and moves down along the wall to be fed via pipe 10 to the degassing device 8. The liquid stream thus obtained then moves via pipe 11 into tube 12 and the determination is performed. Tube 12 is provided with a drain 31.

Figure 3:
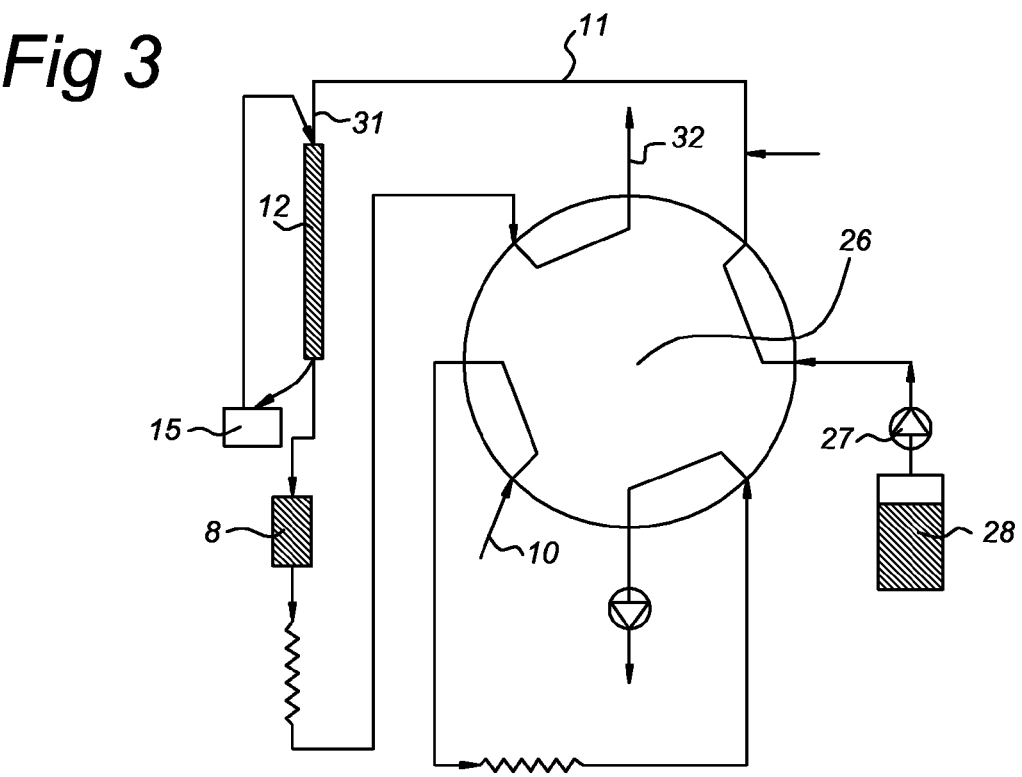
FIG. 3 shows diagrammatically the circuit of the assembly according to the invention during the determination of a sample.
Figure 4:
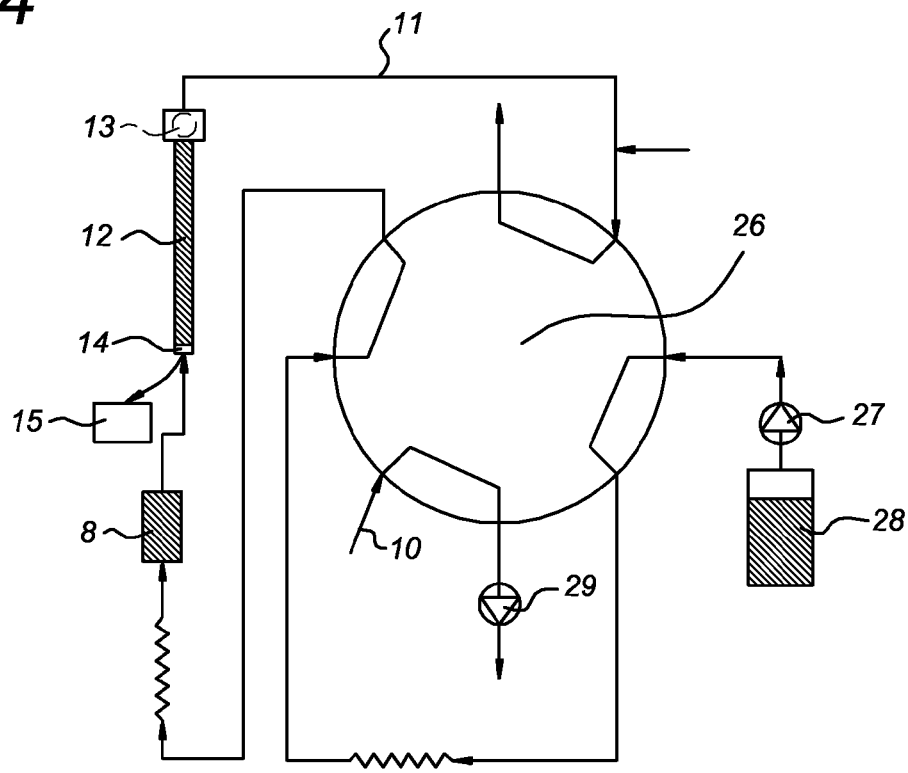
FIG. 4 shows the illustration according to FIG. 3 during the flushing of the device.

FIGS. 3 and 4 show how the measuring tube 12 can be cleaned regularly. For this purpose there is a rotary valve 26 with which different connection options can be effected. In addition, there is a flushing agent in holder 28 which can be pumped via pump 27.

Flushing is performed in the position shown in FIG. 3. The agent is fed from holder 28 via pump 27 to the outlet 31 of the measuring tube 12 and pumped through the measuring tube 12. After passing the degassing device 8, it is discharged as waste at drain 32.

In the measurement position according to FIG. 4, the sample located in the pipe section between 4 and 7 is fed as a package via pipe 10 and pump 27 with the liquid from holder 28 after the degassing to tube 12.

With the assembly described above, it is possible to determine both the absolute soot concentration and a particle size distribution in an accurate manner. If water is used as the solvent, salts disturbing the measurement can be brought into solution. Examples of these are ammonia, sulphate, sodium and nitrogen oxides.

The assembly can be calibrated by any method known in the state of the art. However, according to the invention, ink is more especially used. Another calibration method is chemical oxidation of soot to carbon dioxide and the subsequent determination of carbon dioxide.

With the present invention it is possible to perform a measurement both continuously and discontinuously. Moreover, it is possible to separate the sampling location and the measurement location by a considerable distance. That is to say an air sample can be taken alongside, for example, roads and the amount of soot can be determined in a laboratory at a few or many kilometres further.

On reading the above description, variants of the assembly described above and the associated method will be immediately apparent to persons skilled in the art. These are considered to fall within the scope of the appended claims.

The invention claimed is:

1. A method for determining soot particles in a gas stream, comprising the following steps:
feeding the gas stream having the soot particles therein;
moistening said soot particles in said gas stream;
introducing the moistened soot particles into a liquid that dissolves salt; and
measuring the transmittance of light through the soot particles to thereby determine absolute soot concentration of the soot particles in the gas stream.

2. Method according to claim 1, wherein the vapour is generated by atomising.

3. Method according to claim 1, wherein the moistened soot particles are physically separated from said gas stream.

4. Method according to claim 1, wherein said liquid comprises water.

5. Method according to claim 1, wherein after the preparation of a suspension comprising said liquid and said soot particles at a first location, the optical properties are determined at a second location that is some distance away from said first location.

6. Method according to claim 1, comprising the determination of the soot particle size distribution in said gas stream, wherein for carrying out said method one part of the gas stream is passed through a first filter, followed by a first determination comprising the measurement of the optical properties, said soot particles in said gas stream being moistened and then introduced into a liquid that dissolves salts and the optical properties of said soot particles/liquid suspension are determined, wherein the optical properties comprise the transmittance of light, wherein another part of the gas stream is then passed through a second filter with a different permeability to the first filter for performing a second determination according to a method comprising the measurement of the optical properties, said soot particles in said gas stream being moistened and then introduced into a liquid that dissolves salts and the optical properties of said soot particles/liquid suspension are determined, wherein the optical properties comprise the transmittance of light.

7. Assembly for determining soot particles in a gas stream, comprising a measurement device for measuring the optical properties comprising a device for taking up said soot particles as a suspension in a liquid that dissolves salts and wherein said measurement device is equipped to measure the transmittance of light through said suspension to determine absolute soot concentration of the soot particles in the gas stream, means being arranged upstream of said device for moistening said soot particles in the gas stream.

8. Assembly according to claim 7, wherein said measurement device includes a light transmittance meter (15).

9. Assembly according to claim 7 wherein said means comprise liquid atomising means.

10. Assembly according to claim 8, comprising a cyclone with an inlet situated on the periphery connected to the outlet of the device for moistening the soot particles in said gas stream, a central upward outlet for gas and a central downward outlet connected to the light measurement device.

* * * * *